United States Patent [19]

Mack et al.

[11] Patent Number: Plant 6,388

[45] Date of Patent: Nov. 8, 1988

[54] CHRYSANTHEMUM PLANT NAMED MIRAGE

[75] Inventors: Grace H. Mack, 108 Wahackme Rd., New Canaan, Conn. 06840; William E. Duffett, Salinas, Calif.

[73] Assignee: Grace H. Mack, New Canaan, Conn.

[21] Appl. No.: 3,602

[22] Filed: Jan. 15, 1987

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Mirage particularly characterized by its flat capitulum form; pompon capitulum type; orange-bronze ray floret color; diameter across face of capitulum up to 4 cm at maturity; medium plant height with spreading and prolific branching pattern; average natural season flower date of August 21 in Salinas, Calif. and September 15 in Hightstown, N.J.; uniform seven week photoperiodic flowering response to short days in photoperiodic controlled flowering programs; and by its durable, uniform performance in outside fall flowerings and in spring small pot flowering programs.

3 Drawing Sheets

The present invention comprises a new and distinct cultivar of chrysanthemum, botanically known as *Chrysanthemum morifolium*, Ramat., and referred to by the cultivar name Mirage.

Mirage, identified as 81MO1001, was originated from a cross made by Grace H. Mack in a controlled breeding program in New Canaan, Conn., in 1980.

The female parent of Mirage was the cultivar identified as Bandit, disclosed in U.S. Plant Pat. No. 4,491. The male parent of Mirage was the cultivar identified as Ironsides, disclosed in U.S. Plant Pat. No. 3,896.

Mirage was discovered and selected as one flowering plant within the progeny of the stated cross by William E. Duffett in September 1981, in a controlled environment in Salinas, Calif.

The first act of asexual reproduction of Mirage was accomplished when vegetative cuttings were taken from the initial selection in December 1981 in a controlled environment in Salinas, Calif., by technicians working under formulations established and supervised by William E. Duffett.

Horticultural examination of controlled flowerings of successive plantings has shown that the unique combination of characteristics as herein disclosed for Mirage are firmly fixed and are retained through successive generations of asexual reproduction.

Mirage has not been observed under all possible environmental conditions. The phenotype may vary significantly with variations in environment such as temperature, light intensity, and daylength.

The following observations, measurements and comparisons describe plants grown in controlled open areas in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Mirage, which, in combination, distinguish this chrysanthemum as a new and distinct cultivar:

1. Flat capitulum form.
2. Pompon capitulum type.

3. Orange-bronze ray floret color.
4. Diameter across face of capitulum up to 4 cm at maturity.
5. Medium plant height.
6. Spreading and prolific branching pattern.
7. Average natural season flower date of August 21 in Salinas, Calif., and September 15 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Mirage, with the colors being as nearly true as possible with illustrations of this type. Sheet 1 is a color photograph of Mirage grown as a pinched spray pot mum. Sheet 2 is a black and white photograph of three views of the inflorescence of Mirage. Sheet 3 is a black and white photograph showing the upper and under sides of the leaves of Mirage at three stages of development (mature, intermediate and immature).

Of the commercial cultivars known to the inventors, the most similar in comparison to Mirage is the female parent Bandit. Reference is made to attached Chart A, which compares certain characteristics of Mirage to the same characteristics of Bandit.

Traits similar to both Bandit and Mirage are capitulum form and type, branching pattern, diameter across face of capitulum, and controlled flowering response. Mirage has a vibrant orange-bronze ray floret color, with Bandit having a more dull bronze-red ray floret color. Mirage has a taller plant height and an earlier natural season flowering response than Bandit.

In the following description, color references are made to The Royal Horticultural Society Color Chart. The color values were determined on plant material grown outside in Salinas, Calif. on Aug. 25, 1986.

Classification:

*Botanical.*—*Chrysanthemum morifolium*, Ramat., cv. Mirage.

*Commercial.*—Pompon spray pot mum and garden mum.

Inflorescence

A. Capitulum:

*Form.*—Flat.

*Type.*—Pompon.

*Diameter across face.*—up to 4 cm at maturity.

B. Corolla of ray florets:

*Color (general tonality from a distance of three meters).*—Orange-bronze.

*Color (upper surface).*—167B to 167C, fading to 22A to 22B.

*Color (under surface).*—163C.

*Shape.*—Oblong.

C. Corolla of disc florets.—Not Present.

D. Reproductive organs:

*Androecium.*—Not Present.

*Gynoecium.*—Present on both ray and disc florets.

PLANT

A. General appearance:

*Height.*—Medium.

*Branching pattern.*—Spreading ad prolific.

B. Foliage:

*Color (upper surface).*—137B.

*Color (under surface).*—137C.

*Shape.*—Lobed and serrated.

CHART A

| COMPARISON OF MIRAGE AND BANDIT | | | |
|---|---|---|---|
| | RAY FLORET | CAPITULUM FORM AND | BRANCHING | DIAMETER ACROSS FACE OF CAPIT- |

CHART A-continued

| COMPARISON OF MIRAGE AND BANDIT | | | | |
|---|---|---|---|---|
| CULTIVAR | COLOR | TYPE | PATTERN | ULUM |
| MIRAGE | ORANGE BRONZE | FLAT POMPON | SPREADING AND PROLIFIC | UP TO 4 cm. |
| BANDIT | RED-BRONZE | FLAT POMPON | SPREADING | UP TO 4 cm. |

| CULTIVAR | PLANT HEIGHT | AVERAGE NATURAL SEASON FLOWER DATE SALINAS, CALIFORNIA |
|---|---|---|
| MIRAGE | MEDIUM | AUGUST 21 |
| BANDIT | SHORT | AUGUST 28 |

| CULTIVAR | AVERAGE NATURAL SEASON FLOWER DATE HIGHTSTOWN NEW JERSEY | CONTROLLED RESPONSE |
|---|---|---|
| MIRAGE | SEPTEMBER 15 | 7 WEEKS |
| BANDIT | SEPTEMBER 26 | 7 WEEKS |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

We claim:

1. A new and distinct chrysanthemum plant named Mirage, as described and illustrated, and particularly characterized as to uniqueness by the combined characteristics of flat capitulum form; pompon capitulum type; orange-bronze ray floret color; diameter across face of capitulum of up to 4 cm at maturity; medium plant height with spreading and prolific branching pattern; average natural season flower date of August 21 in Salinas, Calif. and September 15 in Hightstown, N.J.; uniform seven week photoperiodic flowering response to short days in photoperiodic controlled flowering programs; and durable, uniform performance in outside all flowerings and in spring small pot flowering programs.

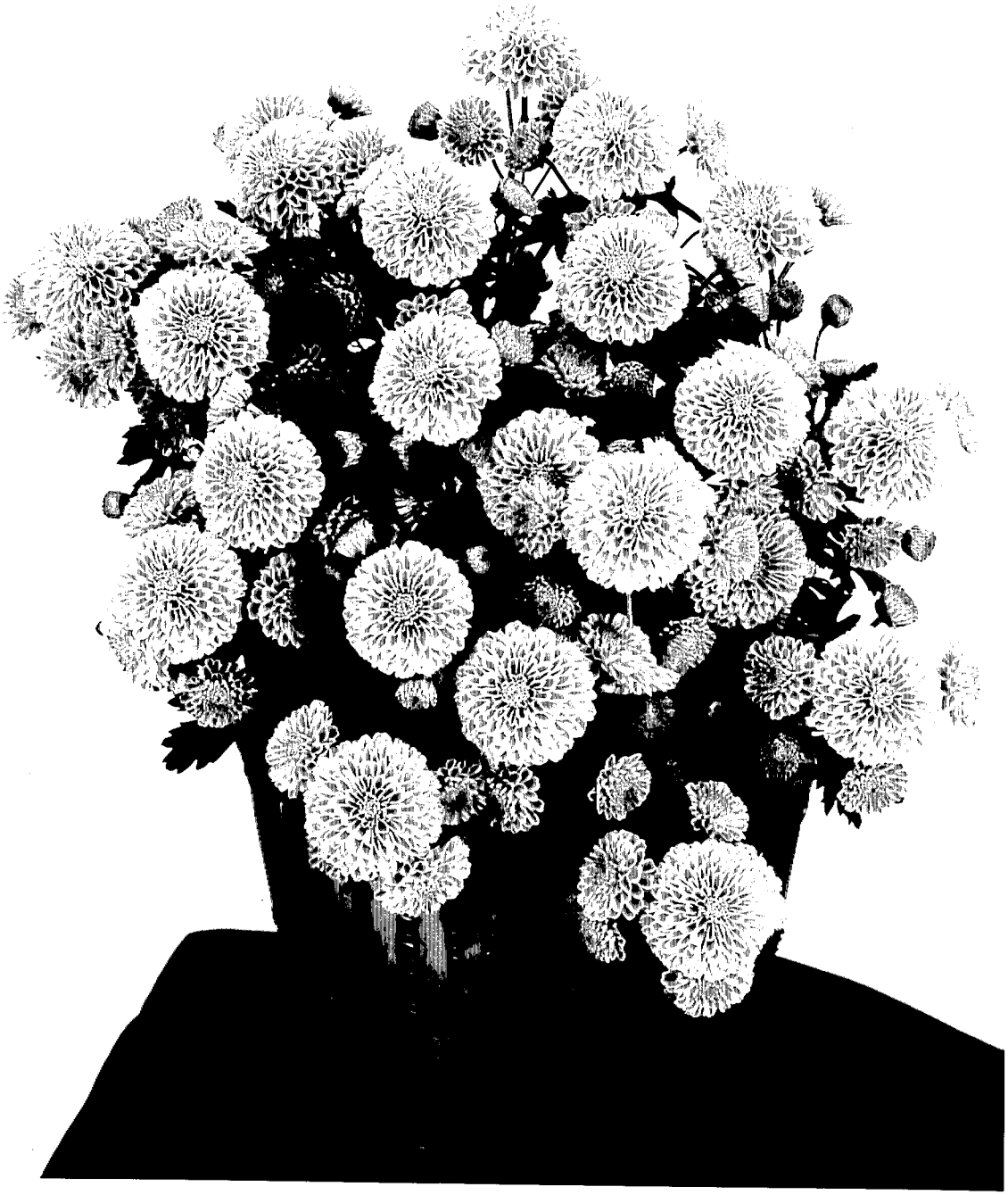

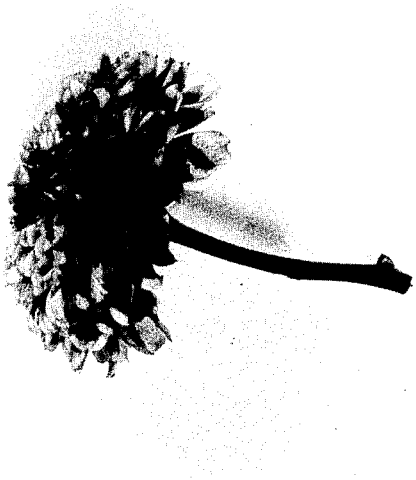
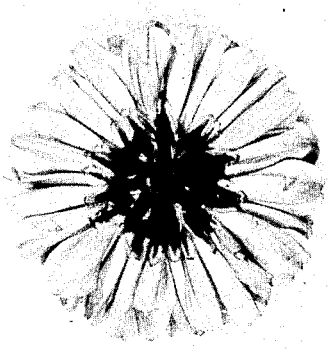
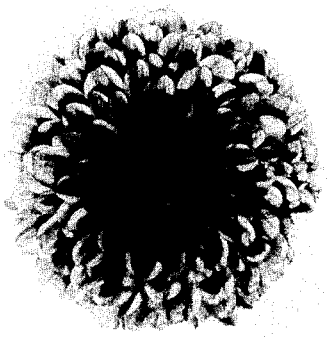

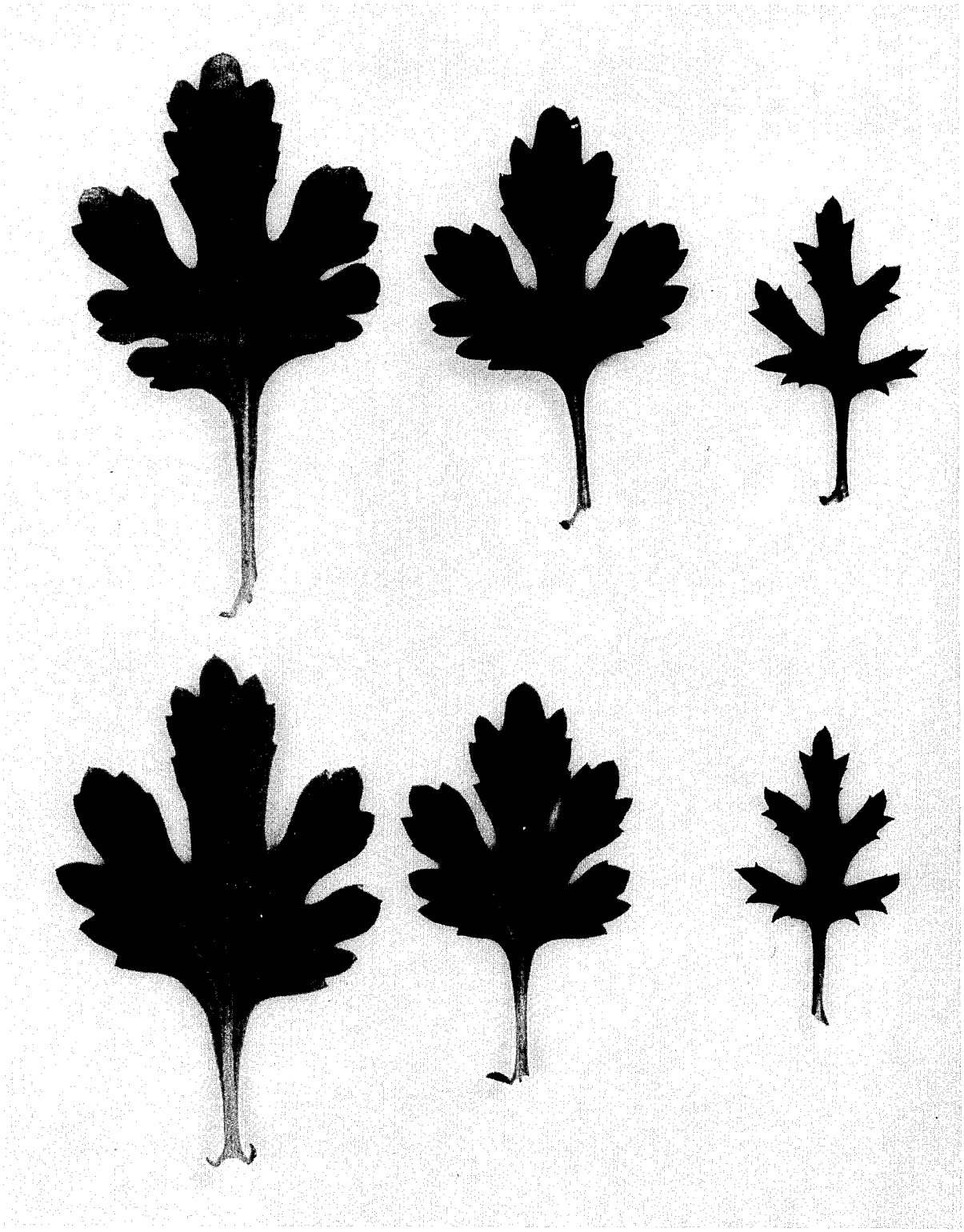

* * * * *